United States Patent
Nakayama et al.

(10) Patent No.: US 10,912,493 B2
(45) Date of Patent: Feb. 9, 2021

(54) SENSOR AND METHOD

(71) Applicant: Panasonic Intellectual Property Management Co., Ltd., Osaka (JP)

(72) Inventors: Takeshi Nakayama, Hyogo (JP); Shoichi Iizuka, Osaka (JP); Naoki Honma, Iwate (JP); Dai Sasakawa, Iwate (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 400 days.

(21) Appl. No.: 15/851,858

(22) Filed: Dec. 22, 2017

(65) Prior Publication Data
US 2018/0192919 A1 Jul. 12, 2018

(30) Foreign Application Priority Data

Jan. 6, 2017 (JP) ................................ 2017-001317
Sep. 20, 2017 (JP) ................................ 2017-180438

(51) Int. Cl.
*A61B 5/11* (2006.01)
*G01S 13/42* (2006.01)
(Continued)

(52) U.S. Cl.
CPC .......... *A61B 5/1116* (2013.01); *A61B 5/0507* (2013.01); *A61B 5/1113* (2013.01);
(Continued)

(58) Field of Classification Search
None
See application file for complete search history.

(56) References Cited

U.S. PATENT DOCUMENTS

| 8,068,051 B1* | 11/2011 | Osterweil ............. A61B 5/1117 340/573.1 |
| 2010/0130873 A1* | 5/2010 | Yuen .................... A61B 5/0022 600/484 |

(Continued)

FOREIGN PATENT DOCUMENTS

| JP | 2001-159678 | 6/2001 |
| JP | 2004-340729 | 12/2004 |

(Continued)

*Primary Examiner* — Whitney Moore
(74) *Attorney, Agent, or Firm* — Greenblum & Bernstein, P.L.C.

(57) ABSTRACT

A sensor includes: a transmitting antenna with N transmitting antenna elements transmitting transmission signals; a receiving antenna with M receiving antenna elements, each receiving N received signals including a reflection signal generated by the living body reflecting part of the N transmission signals; a circuit; and a memory. The circuit extracts a second matrix corresponding to a specified frequency range from an N×M first matrix calculated from each received signal and indicating a propagation property between each transmitting antenna element and each receiving antenna element, estimates the position where the living body is present using the second matrix, calculates a radar cross-section (RCS) value of the living body based on the estimated position and the positions of the transmission and receiving antennas, and estimates the motion of the living body using the calculated RCS value and information indicating correspondence between RCS values and motions of the living body.

13 Claims, 10 Drawing Sheets

(51) Int. Cl.

| | |
|---|---|
| *G01S 7/41* | (2006.01) |
| *A61B 5/05* | (2006.01) |
| *G01S 13/88* | (2006.01) |
| *G01S 13/89* | (2006.01) |
| *G01S 13/00* | (2006.01) |
| *G01B 15/00* | (2006.01) |
| *A61B 5/024* | (2006.01) |
| *A61B 5/08* | (2006.01) |
| *A61B 5/0507* | (2021.01) |

(52) U.S. Cl.
CPC ............. *A61B 5/1117* (2013.01); *G01S 7/411* (2013.01); *G01S 7/415* (2013.01); *G01S 13/003* (2013.01); *G01S 13/42* (2013.01); *G01S 13/88* (2013.01); *G01S 13/89* (2013.01); *A61B 5/024* (2013.01); *A61B 5/0816* (2013.01); *A61B 2562/0228* (2013.01); *A61B 2562/046* (2013.01); *G01B 15/00* (2013.01)

(56) References Cited

U.S. PATENT DOCUMENTS

2017/0215772 A1* 8/2017 Garn .................... A61B 5/08
2019/0056422 A1* 2/2019 Park .................... A63F 13/212

FOREIGN PATENT DOCUMENTS

| JP | 2006-081771 | 3/2006 |
|---|---|---|
| JP | 2013-160730 | 8/2013 |
| JP | 2014-190724 | 10/2014 |
| JP | 2015-184149 | 10/2015 |
| JP | 2016-135233 | 7/2016 |

* cited by examiner

| | MOTION | | | |
|---|---|---|---|---|
| | FALLING DOWN | SITTING ON CHAIR | SITTING ON FLOOR | STANDING UP FROM CHAIR |
| MODEL CODE | MODEL CODE 1 | MODEL CODE 2 | MODEL CODE 3 | MODEL CODE 4 |
| | MOTION | | | |
| | STANDING UP FROM FLOOR | JUMPING | TURNING DIRECTION | |
| MODEL CODE | MODEL CODE 5 | MODEL CODE 6 | MODEL CODE 7 | |

SENSOR AND METHOD

BACKGROUND

1. Technical Field

The present disclosure relates to a sensor and a method of estimating actions of a living body using microwaves.

2. Description of the Related Art

As methods to identify the position and the action of a person, methods using microwaves have been studied (for example, see Japanese Unexamined Patent Application Publication Nos. 2015-184149, 2006-81771, 2001-159678, 2013-160730, 2004-340729, 2014-190724, and 2016-135233). Specifically, Japanese Unexamined Patent Application Publication No. 2015-184149 discloses a method of judging whether a person is present by monitoring the motion of the person using the change amount of a received signal. Japanese Unexamined Patent Application Publication No. 2006-81771 discloses a method of identifying the head and the limbs of a living body, using THz waves. Japanese Unexamined Patent Application Publication No. 2001-159678 discloses a method of estimating the size of a target, using a radio wave radar. Japanese Unexamined Patent Application Publication No. 2013-160730 discloses a method of measuring the trace of a target, using a millimeter wave radar. Japanese Unexamined Patent Application Publication No. 2004-340729 discloses a method of judging whether a target is a person, by RCS measurement with a Doppler radar. Japanese Unexamined Patent Application Publication No. 2014-190724 discloses a method of estimating the position and the state of a living body by machine learning, using channel information of multiple antennas and various sensor information. Japanese Unexamined Patent Application Publication No. 2016-135233 discloses a method of determining which of a lying position and a sitting position a person is taking, based on the measurement result of an FMCW radar.

However, to improve the accuracy of estimating the motion of a living body using microwaves, further improvements are required.

SUMMARY

In one general aspect, the techniques disclosed here feature a sensor including: a transmitting antenna including N transmitting antenna elements, each of which transmits a transmission signal to a specified area where a living body can be present, N being a natural number of 3 or more; a receiving antenna including M receiving antenna elements, each of which receives N received signals including a reflection signal which the living body generates by reflecting part of the N transmission signals transmitted by the N transmitting antenna elements, M being a natural number of 3 or more; a circuit; and a memory which stores correspondence information indicating correspondence of a motion of the living body with temporal changes of a radar cross-section value and a vertical position which is a position in a vertical direction at which the living body is present relative to the sensor, in which at least three transmitting antenna elements of the N transmitting antenna elements are arranged in positions different in the vertical direction and a horizontal direction, at least three receiving antenna elements of the M receiving antenna elements are arranged in positions different in the vertical direction and a horizontal direction, and the circuit calculates an N×M first matrix with components, each of which is a complex transfer function indicating a propagation property between each of the N transmitting antenna elements and each of the M receiving antenna elements, from each of the N received signals received by each of the M receiving antenna elements during a specified period, extracts a second matrix corresponding to a specified frequency range in the first matrix, the second matrix corresponding to components affected by a vital activity including at least one of respiration, heartbeats, and body motion of the living body, estimates a three-dimensional position at which the living body is present relative to the sensor, using the second matrix, the three-dimensional position including the vertical position, calculates a first distance indicating a distance between the living body and the transmitting antenna and a second distance indicating a distance between the living body and the receiving antenna, based on the estimated three-dimensional position, a position of the transmitting antenna, and a position of the receiving antenna, calculates a radar cross-section value of the living body, using the first distance and the second distance, and estimates a motion of the living body, using temporal changes of the estimated three-dimensional position and the calculated radar cross-section value, and the correspondence information stored in the memory.

The present disclosure makes it possible to estimate the motion of a living body in a short time with high accuracy by using microwaves.

These general and specific aspects may be implemented using a system, a method, and a computer program, and any combination of systems, methods, and computer programs.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

Figure 1:
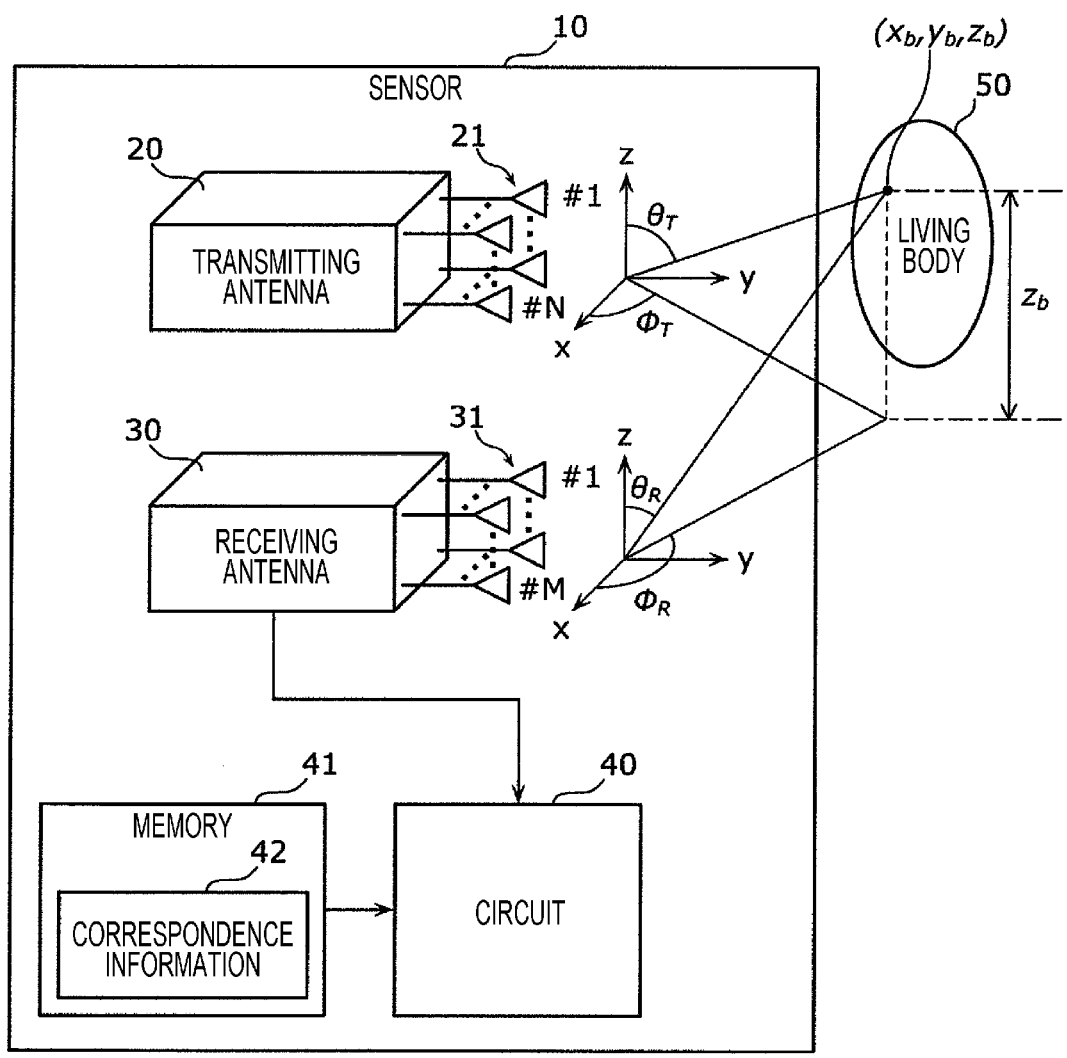
FIG. 1 is a block diagram illustrating an example of the configuration of a sensor according to an embodiment.

DETAILED DESCRIPTION (Underlying Knowledge Forming Basis of the Present Disclosure)

The inventors studied in detail the related arts concerning state estimation of a living body using microwaves. As a result, the inventors found that the method in Japanese Unexamined Patent Application Publication No. 2015-184149 can detect whether a person is present, but that the method has a problem that it is difficult to detect the direction, position, state, motion, and the like of the person.

The inventors found that the method in Japanese Unexamined Patent Application Publication No. 2006-81771 can detect the head and the limbs of a person and estimate the direction, position, and state and the like of the person, but that the method has a problem that the cost is high because of the use of a terahertz band device.

The inventors found that the method in Japanese Unexamined Patent Application Publication No. 2001-159678 can estimate the size of a target, but that the method has a problem that it is difficult to estimate the state of a living body that is a person or the like.

The inventors found that the method in Japanese Unexamined Patent Application Publication No. 2013-160730 can estimate the trace of the position of a target living body, but that the method has a problem that it is difficult to estimate the state of the living body.

The inventors found that the method in Japanese Unexamined Patent Application Publication No. 2004-340729 can estimate whether a target is a person, using RCS, but that the method has a problem that it is difficult to estimate the state of the living body that is a person or the like.

The inventors found that Japanese Unexamined Patent Application Publication No. 2014-190724 has a problem that machine learning is required for each user.

The inventors found that Japanese Unexamined Patent Application Publication No. 2016-135233 has a problem that it is difficult to estimate the motion of a person.

As results of repeated research on the above problems, the inventors found out that it is possible to estimate the direction, position, size, posture, motion, and the like of a living body in a short time with high accuracy, by using propagation properties and the Rader Cross Section of reflection signals, which the living body generates by reflecting signals transmitted from a transmitting antenna including multiple antenna elements arranged at positions different in the vertical direction and horizontal direction. This finding led to the present disclosure.

To estimate the position of a living body at rest, data of several seconds are necessary to estimate the motion of a living body because the position is estimated mainly based on components derived from respiration and heartbeats of the living body which occur in a cycle of a few seconds. Meanwhile, in order to estimate a quick motion such as falling down it was found that it is necessary to use data of a short time, less than 1 second, because the quick motion is estimated based on components derived from body motion of the living body with a duration of less than 1 second, and in order to estimate the posture of a living body at rest, the posture of a living body in motion, and the posture of a living body both at rest and in motion, it was found that it is necessary to use different time data lengths for data of a single measurement to estimate the position and the posture of the living body.

(1) A sensor according an aspect of the present disclosure is a sensor including: a transmitting antenna including N transmitting antenna elements, each of which transmits a transmission signal to a specified area where a living body can be present, N being a natural number of 3 or more; a receiving antenna including M receiving antenna elements, each of which receives N received signals including a reflection signal which the living body generates by reflecting part of the N transmission signals transmitted by the N transmitting antenna elements, M being a natural number of 3 or more; a circuit; and a memory which stores correspondence information indicating correspondence of a motion of the living body with temporal changes of a radar cross-section value and a vertical position which is a position in a vertical direction at which the living body is present relative to the sensor, in which at least three transmitting antenna elements of the N transmitting antenna elements are arranged in positions different in the vertical direction and a horizontal direction, at least three receiving antenna elements of the M receiving antenna elements are arranged in positions different in the vertical direction and a horizontal direction, and the circuit calculates an N×M first matrix with components, each of which is a complex transfer function indicating a propagation property between each of the N transmitting antenna elements and each of the M receiving antenna elements, from each of the N received signals received by each of the M receiving antenna elements during a specified period, extracts a second matrix corresponding to a specified frequency range in the first matrix, the second matrix corresponding to components affected by a vital activity including at least one of respiration, heartbeats, and body motion of the living body, estimates a three-dimensional position at which the living body is present relative to the sensor, using the second matrix, the three-dimensional position including the vertical position, calculates a first distance indicating a distance between the living body and the transmitting antenna and a second distance indicating a distance between the living body and the receiving antenna, based on the estimated three-dimensional position, a position of the transmitting antenna, and a position of the receiving antenna, calculates a radar cross-section value of the living body, using the first distance and the second distance, and estimates a motion of the living body, using temporal changes of the estimated three-dimensional position and the calculated radar cross-section value, and the correspondence information stored in the memory.

This configuration makes it possible to estimate the motion of a living body in a short time with high accuracy using microwaves.

(2) In the above aspect, the motion of the living body associated in the correspondence information may include falling down, sitting on a chair, sitting on a floor, standing up from a chair, standing up from a floor, jumping, and turning direction, and the circuit may estimate which motion the living body is performing, out of the falling down, sitting on a chair, sitting on a floor, standing up from a chair, standing up from a floor, jumping, and turning direction, using the temporal changes of the estimated three-dimensional position and the calculated radar cross-section value and the correspondence information stored in the memory.

This configuration makes it possible to estimate the motion of a living body in a shorter time.

(3) In the above aspect, in estimating the motion of the living body, the circuit may extract a period in which the temporal change of the estimated vertical position or the calculated radar cross-section value is larger than a predetermined value, as a motion period in which the living body is in motion, and may estimate the motion of the living body, using the temporal changes of the estimated three-dimensional position and the calculated radar cross-section value during the extracted motion period, and the correspondence information stored in the memory.

This configuration makes it possible to reduce a processing load involved in estimating the motion of a living body.

(4) In the above aspect, the circuit may extract the motion period, using time series data obtained from a plurality of the vertical positions or a plurality of the radar cross-section values obtained in time series by removing an instantaneous noise component using a predetermined filter.

This configuration makes it possible to estimate the motion of a living body with higher accuracy.

(5) In the above aspect, the vertical position and the radar cross-section value which are associated with the motion of the living body in the correspondence information may be expressed by a direction code which is obtained by normalizing a direction vector into which the temporal changes of the vertical position estimated by the circuit and the radar cross-section value calculated by the circuit in advance when the living body performs one motion as the motion of the living body in the specified area are converted by using a predetermined method, and in estimating the motion of the living body, the circuit may convert the temporal changes of the vertical position obtained from the estimated three-dimensional position and the calculated radar cross-section value during the extracted motion period into a direction vector using a predetermined method, calculate a direction code by normalizing the direction vector obtained from conversion, and estimate the motion of the living body using the calculated direction code and the corresponding information.

This configuration makes it possible to estimate the motion of a living body with higher accuracy.

(6) In the above aspect, the circuit may estimate the motion of the living body during a second motion period next to a first motion period, using a posture of the living body at the end of the first motion period.

This makes it possible to estimate the next motion of a living body, utilizing an estimated motion of the living body. This allows for efficient estimation of the motion of a living body.

(7) In the above aspect, when a variation in a horizontal direction of the estimated three-dimensional position is larger than or equal to a predetermined distance, the circuit may further estimate that the living body is moving in the horizontal direction.

This configuration makes it possible to estimate the movement of a living body in the horizontal direction in a short time with high accuracy.

(8) In the above aspect, the circuit may further estimate a height of the living body, using the vertical position included in the three-dimensional position from which the living body is estimated to be moving in the horizontal direction.

This configuration makes it possible to estimate the height of a living body in a short time with high accuracy. Hence, for example, if multiple living bodies which can be present in a specified area are known in advance, and the heights of the multiple living bodies are different, this method can be utilized to identify which living body of the multiple living bodies is present and in motion.

(9) In the above aspect, the circuit may further estimate a body size of the living body, using the radar cross-section value calculated when the living body is estimated to be moving in the horizontal direction.

This configuration makes it possible to estimate the body size of a living body in a short time with high accuracy. Hence, for example, if multiple living bodies which can be present in a specified area are known in advance, and the body sizes of the multiple living bodies are different, this method can be utilized to identify which living body of the multiple living bodies is present and in motion.

(10) In the above aspect, the specified period may be about half a cycle of at least one of respiration, heartbeats, and body motion of the living body.

This makes it possible to estimate the motion of a living body efficiently.

Note that not only may the present disclosure be implemented as a sensor, but the present disclosure may be implemented as an integrated circuit device including processing means included in such a sensor; as a method having the processing means included in the device, as steps; as a program executed by a computer and including these steps; and as information, data, or signals indicating the program. These program, information, data, and signals may be distributed via a recording medium such as a CD-ROM or a communication medium such as the Internet.

Hereinafter, an embodiment of the present disclosure will be described in detail using the drawings. Note that each of the embodiments described below is for illustrating a specific preferred example. Values, shapes, materials, constituents, arrangements and connection methods of constituents, steps, the orders of steps, and the like shown in the embodiment below are mere examples and are not intended to limit the present disclosure. In addition, of the constituents in the following embodiments, the constituents which are not recited in independent claims showing the highest level concept are described as optional constituents to constitute more preferred embodiments. Note that in this specification and the drawings, constituents having substantially the same functional configurations are denoted by the same symbols, and repetitive descriptions thereof will be omitted.

Embodiment

Figure 3:
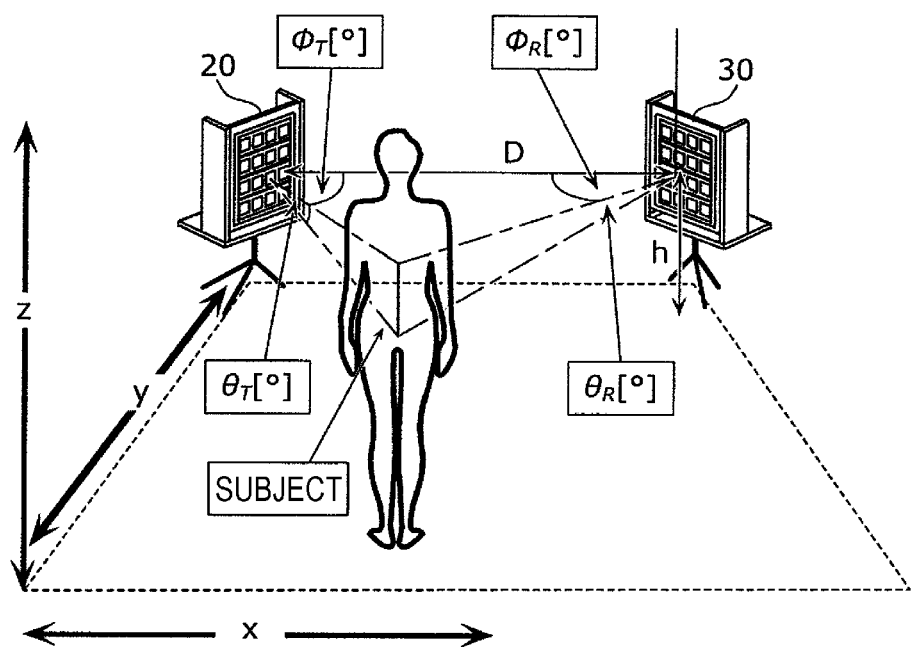
FIG. 3 is a diagram illustrating an installation example of the sensor according to the embodiment.

FIG. 1 is a block diagram illustrating an example of the configuration of a sensor according to an embodiment. FIG. 3 is a diagram illustrating an installation example of the sensor according to the embodiment.

As illustrated in FIG. 1, a sensor 10 includes a transmitting antenna 20, a receiving antenna 30, circuit 40, and memory 41. The sensor 10 emits microwaves to a living body 50, such as a human, from the transmitting antenna 20 and receives the reflected waves reflected from the living body 50 with the receiving antenna 30. Here, $\varphi_T$ is an angle formed between a first reference direction which is a direction on the horizontal plane and arbitrarily set relative to the transmitting antenna 20, and a first living body direction which is a direction from the transmitting antenna 20 toward the living body 50. $\theta_T$ is an elevation angle of the living body 50 formed between the vertical direction and the first living body direction. $\varphi_R$ is an elevation angle of the living body 50 formed between a second reference direction which is a direction on the horizontal plane and arbitrarily set relative to the receiving antenna 30, and a second living body direction which is a direction from the receiving antenna 30 toward the living body 50. $\theta_R$ is an angle formed between the vertical direction and the second living body direction.

When $(x_b, y_b, z_b)$ is the center coordinates of a part at which the living body 50 performs vital activities, the directions $(\theta_T, \theta_R, \varphi_T, \varphi_R)$ and the coordinates $(x_b, y_b, z_b)$ can be mutually converted according to the positional relationship between the transmitting antenna 20, the receiving antenna 30, and the living body 50.

The transmitting antenna 20 includes N transmitting antenna elements 21. The transmitting antenna 20 has an array antenna in which $N_x$ transmitting antenna elements 21 line in the horizontal direction (x direction) and $N_z$ transmitting antenna elements 21 in the vertical direction (z direction) so that N ($N_x \times N_z$) transmitting antenna elements 21 are arranged in a rectangular shape. In other words, at least three transmitting antenna elements 21 of the N transmitting antenna elements 21 are arranged at positions different in the vertical direction and the horizontal direction. Each of the N transmitting antenna elements 21 transmits a transmission signal to a specified area where a living body can be present. In other words, the transmitting antenna 20 transmits N transmission signals to the specified area from N different positions. Note that the specified area where a living body can be present means a detection area where the sensor 10 detects the existence of a living body.

Specifically, Each of the N transmitting antenna elements 21 emits microwaves as a transmission signal to the living body 50, such as a human. The N transmitting antenna elements 21 may transmit as transmission signals, signals subjected to different modulation processing for each antenna element 21. Each of the N transmitting antenna elements 21 may sequentially switch a modulated signal and an unmodulated signal to transmit. The modulation processing may be performed by the transmitting antenna 20. By making the transmission signals transmitted from the N transmitting antenna elements 21 different from each other for each of the N transmitting antenna elements 21 as described above, it is possible to identify from a transmission signal received by the receiving antenna 30, the transmitting antenna element 21 which transmitted the transmission signal. As above, the transmitting antenna 20 may include a circuit for performing modulation processing.

The receiving antenna 30 includes M receiving antenna elements 31. The receiving antenna 30 has an array antenna in which $M_x$ receiving antenna elements 31 line in the horizontal direction (x direction) and $M_z$ receiving antenna elements 31 in the vertical direction (z direction) so that M ($M_x \times M_z$) receiving antenna elements 31 are arranged in a rectangular shape. In other words, at least three receiving antenna elements 31 of the M receiving antenna elements 31 are arranged at positions different in the vertical direction and the horizontal direction. Each of the M receiving antenna elements 31 receives N received signals including reflection signals which are signals reflected by the living body 50 out of the N transmission signals. The receiving antenna 30 frequency-converts the received signals, which are microwaves, into low frequency signals. The receiving antenna 30 outputs to the circuit 40 the signals obtained from the conversion into the low frequency signals. In other words, the receiving antenna 30 may include a circuit for processing the received signals.

The circuit 40 performs various processing to operate the sensor 10. The circuit 40, for example, includes a processor which executes a control program and a volatile storage area (main storage apparatus) used as a work area when the control program is executed. The volatile storage area is, for example, a random access memory (RAM). Note that the circuit 40 may be constituted of a dedicated circuit for performing various processing to operate the sensor 10. In other words, the circuit 40 may be a circuit performing software processing or a circuit performing hardware processing.

The memory 41 is a nonvolatile storage area (auxiliary storage apparatus), such as a read only memory (ROM), flash memory, or hard disk drive (HDD). The memory 41 stores, for example, information utilized for various processing to operate the sensor 10.

Next, the functional configuration of the circuit 40 will be described using FIG. 2.

Figure 2:
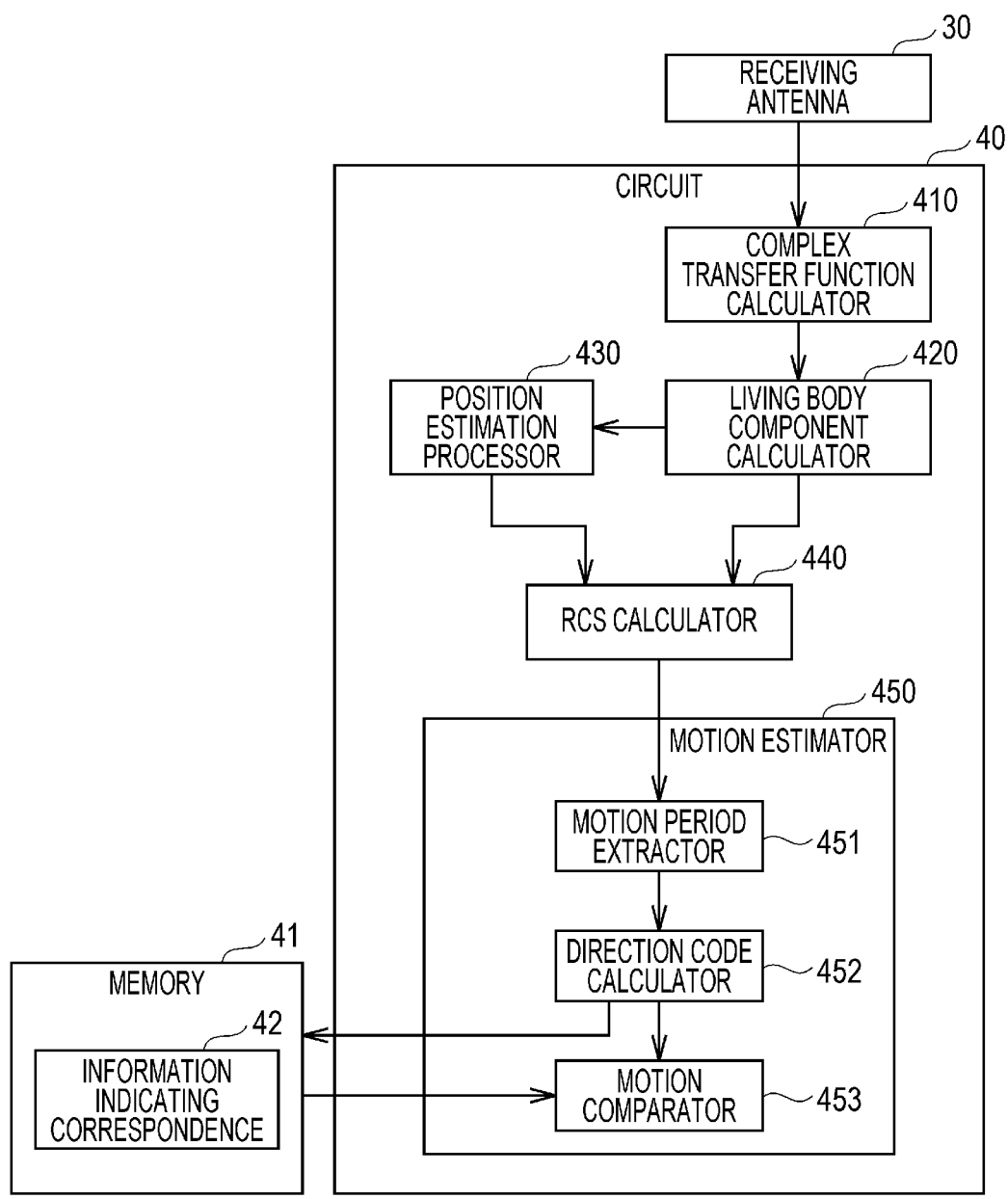
FIG. 2 is a block diagram illustrating the functional configurations of a circuit and a memory according to the embodiment.

FIG. 2 is a block diagram illustrating the functional configuration of the circuit and the memory according to the embodiment.

The circuit 40 includes a complex transfer function calculator 410, a living body component calculator 420, a position estimation processor 430, an RCS calculator 440, and a motion estimator 450.

The complex transfer function calculator 410 calculates a complex transfer function from the low frequency signal into which the received signal has been converted. The complex transfer function indicates propagation loss and phase rotation between each transmitting antenna element 21 and each receiving antenna element 31. In the case where the number of the transmitting antenna elements is N and the number of the receiving antenna elements is M, the complex transfer function is a complex matrix with M×N components. Hereinafter, this complex matrix is referred to as a complex transfer function matrix. The estimated complex transfer function matrix is outputted to the living body component calculator 420. In other words, the complex transfer function calculator 410 calculates an N×M first matrix with the components, each of which is a complex transfer function indicating a propagation property between each of the N transmitting antenna elements 21 and each of the M receiving antenna elements 31, from each of the multiple received signals received by all the M receiving antenna elements 31 during a specified period.

The living body component calculator 420 separates the components into complex transfer function matrix components obtained from the received signals received via the living body 50 and complex transfer function matrix components obtained from the receptions signals received not via the living body 50. The components via the living body 50 means components which vary with time due to the biological activities. Hence, assuming, for example, that things other than the living body 50 remain stationary, the components via the living body 50 can be extracted by taking out components other than direct current from the components obtained by Fourier transforming the components of the complex transfer function matrix in the time direction. Alternatively, the components via the living body 50 can also be extracted, for example, by taking out the components of which the differences from the results measured when the living body 50 was not present in the specified area exceed a predetermined threshold. In this way, the living body component calculator 420 calculates the extracted complex transfer function matrix components as living body components, by extracting the complex transfer function matrix components obtained from the received signals including the reflection signals via the living body 50. In other words, the living body component calculator 420 extracts a second matrix corresponding to a specified frequency range in the first matrix, the second matrix corresponding to the components affected by vital activities including at least one of respiration, heartbeats, and body motion of the living body. The specified frequency range, for example, includes frequencies derived from the vital activities described above including at least one of respiration, heartbeats, and body motion of the living body. The specified frequency range is, for example, from 0.1 to 3 Hz inclusive. This frequency range makes it possible to extract living body components affected by vital activities at a part of living body 50 by the movement of the heart, lungs, diaphragm or other internal organs, or vital activities of the hands and the legs. Note that a part of living body 50 by the movement of the heart, lungs, diaphragm, or other internal organs is, for example, the pit of the stomach of a human.

Here, the living body components are a matrix with M×N components, which are extracted from the complex transfer functions obtained from the received signals measured by the receiving antenna 30 during the specified period. For this reason, it is assumed that the living body components include a frequency response or time response information. Note that the specified period is about half the cycle of at least one of respiration, heartbeats, and body motion of the living body.

The living body components calculated by the living body component calculator 420 are outputted to the position estimation processor 430. The position estimation processor 430 estimates the position of the living body using the calculated living body components. In other words, using the second matrix, the position estimation processor 430 estimates the three-dimensional position where the living body 50 is present relative to the sensor 10, the three-dimensional position including the vertical position of the living body relative to the sensor 10. To estimate the position estimation, both departure angle $\theta_T$ from the transmitting antenna 20 and arrival angle $\theta_R$ to the receiving antenna 30 are estimated, and then the position of the living body 50 is estimated by triangulation using the estimated departure angle $\theta_T$ and arrival angle $\theta_R$.

Note that as for the position estimation, in the case where a first distance between the living body 50 to be measured and the transmitting antenna 20 or a second distance between the living body 50 and the receiving antenna 30 is so small as to be the same as the aperture of the array antenna included in the transmitting antenna 20 or the receiving antenna 30, it is possible to use what is called spherical mode vectors to estimate the position of the living body 50. This is because the departure angles from and the arrival angles to the array antenna elements are different for each array antenna element included in the transmitting antenna 20 or the receiving antenna 30. Since it is impossible in this case to define a departure angle and an arrival angle unlike the plane waves, steering vectors described later are defined using two dimensional or three-dimensional coordinates indicating the positional relationships between the target living body 50 and the array antenna elements included in the transmitting antenna 20 or the receiving antenna 30.

Note that depending on the purpose, the position estimation processor 430 may estimate the position of the living body 50 at rest from measurement data obtained by measuring during a first measurement period which is, for example, 3 seconds or more, and in addition also estimate the position of the living body 50 in motion using measurement data obtained by measuring during a second measurement period which is shorter than the first measurement period, such as 1 second, or 0.5 seconds, for example. The concept of this case is illustrated in FIGS. 4A and 4B.

Figure 4A:
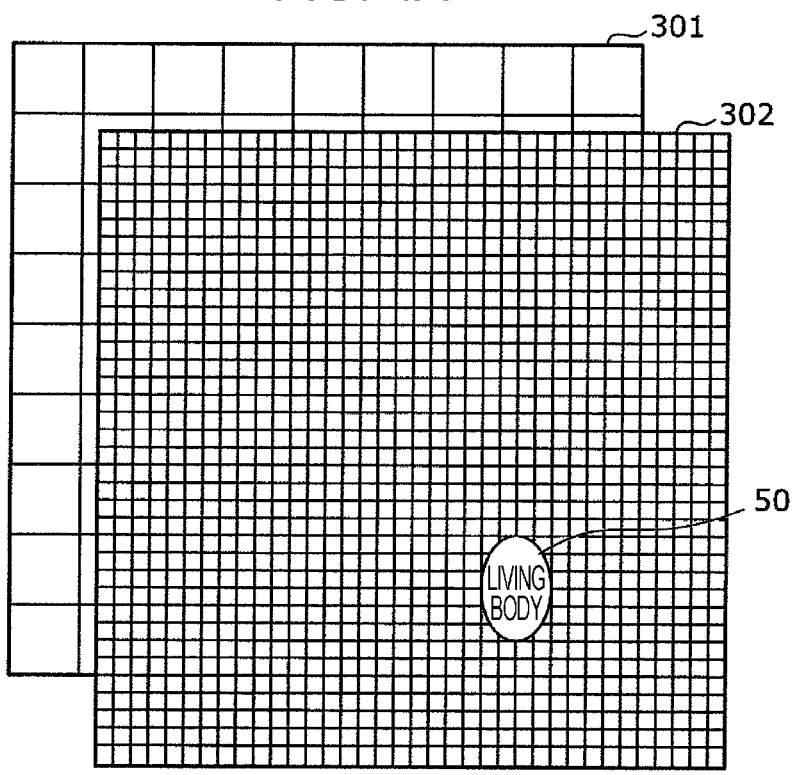
FIG. 4A is a diagram for explaining an example of position resolution of a sensor measuring during different measurement periods.
Figure 4B:
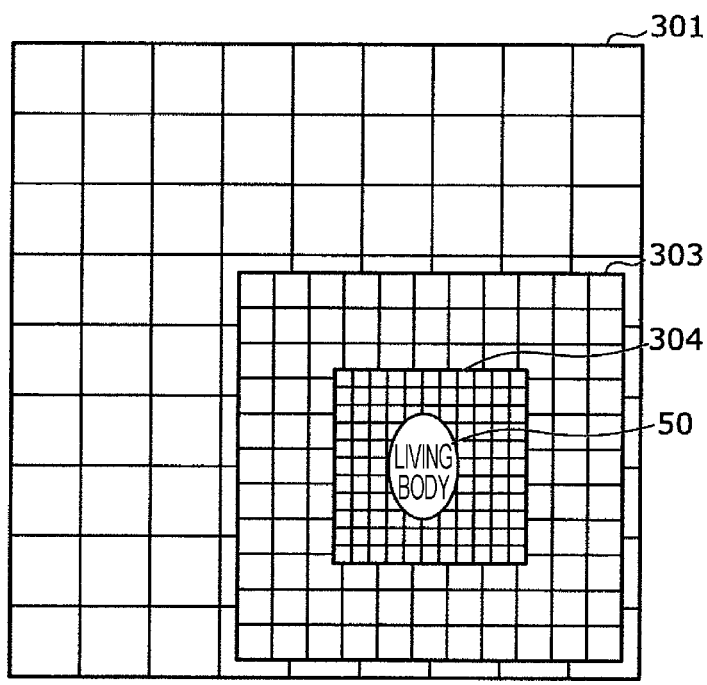
FIG. 4B is a diagram explaining another example of position resolution of a sensor measuring during different measurement periods.

FIG. 4A is a diagram for explaining an example of position resolution of a sensor measuring during different measurement periods.

As illustrated in FIG. 4A, for example, in the case where the entire area of a lattice 301 including multiple quadrangle areas, for example, indicates a specified area which is the measurement area of the sensor 10, and the area is a space of 8 m×8 m, the area shows multiple areas which are measured during the first measurement period at a resolution of 100 cm square. In addition, in the case where the entire area of a lattice 302 including multiple quadrangle areas indicates a specified area which is the measurement area of the sensor 10, and the area is a space of 8 m×8 m which is the same as the lattice 301, the area shows multiple areas which are measured during the second measurement period at a resolution of 5 cm square. As described above, the first measurement period is, for example, 3 seconds, and the second measurement period is, for example, 0.5 seconds. A first period taken to measure each of the multiple areas partitioned by the lattice 301 during the first measurement period and a second period taken to measure each of the multiple areas partitioned by the lattice 302 during for the second measurement period overlap each other. In other words, processing to measure each of the multiple areas partitioned by the lattice 301 and processing to measure each of the multiple areas partitioned by the lattice 302 are executed by parallel processing.

Processing to measure the living body 50 during different measurement periods may be executed as follows.

FIG. 4B is a diagram for explaining another example of position resolution of a sensor measuring during different measurement periods.

As illustrated in FIG. 4B, for example, in the case where the entire area of the lattice 301 including the multiple quadrangle areas indicates a specified area which is the measurement area of the sensor 10 and is a space of 8 m×8 m in the same way as in the explanation for FIG. 4A, the area shows multiple areas which are measured during the first measurement period at a resolution of 100 cm square. The entire area of a lattice 303 including multiple quadrangle areas shows multiple areas which are measured during the second measurement period at a resolution of 30 cm square in a space of 4 m×4 m which is the area including the position of the living body 50 detected by the measurement using the multiple areas of the lattice 301. In addition, the entire area of a lattice 304 including multiple quadrangle areas shows multiple areas which are measured during a third measurement period shorter than the second measurement period at a resolution of 10 cm square in a space of 2 m×2 m which is the area including the position of the living body 50 detected by the measurement using the multiple areas of the lattice 303. The first measurement period is, for example, 3 seconds, the second measurement period is, for example, 1 second, and the third measurement period is, for example, 0.5 seconds. Note that to improve the detection accuracy of the position of the living body 50 at rest, the first measurement period may be set to a time longer than 3 seconds, such as 10 to 20 seconds.

The RCS calculator 440 calculates the Rader Cross Section (RCS: Radar Cross Section) using the living body components and the estimated position. Specifically, to calculate the scattering cross section, the RCS calculator 440 calculates distance RT indicating the first distance between the living body 50 and the transmitting antenna 20 and distance RR indicating the second distance between the living body 50 and the receiving antenna 30 based on the estimated three-dimensional position, the position of the transmitting antenna 20, and the position of the receiving antenna 30. The RCS calculator 440 calculates a propagation distance from the calculated distance RT and distance RR and calculates the RCS using the calculated propagation distance and the intensity of the living body components. Note that the positions of the transmitting antenna 20 and the receiving antenna 30 may be stored in advance in the memory 41.

The motion estimator 450 estimates the motion of the living body 50 using time series data indicating temporal changes of the three-dimensional position estimated by the position estimation processor 430 and the RCS value calculated by the RCS calculator 440, and correspondence information 42 stored in advance in the memory 41. The motion estimator 450 includes a motion period extractor 451, a direction code calculator 452, and a motion comparator 453.

Figure 5:
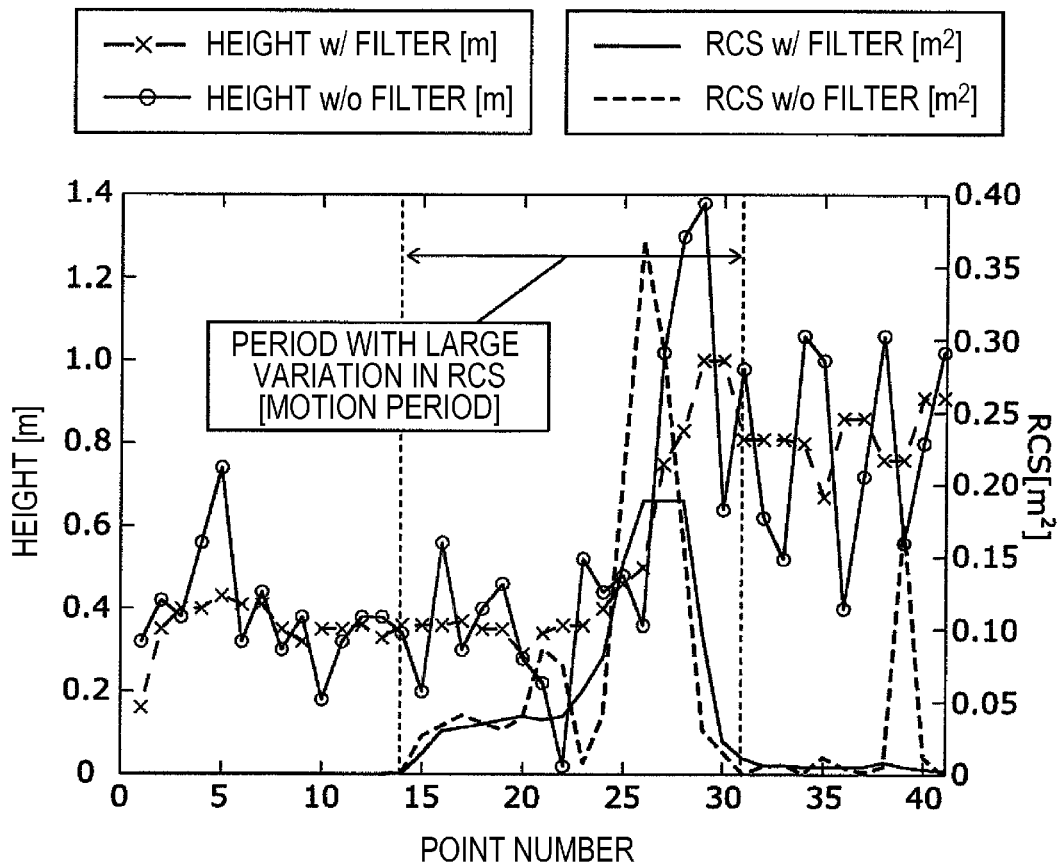
FIG. 5 is a graph for explaining an example of extracting a motion period from time series data of a height position (Height) or an RCS value.

As illustrated in FIG. 5, the motion period extractor 451 extracts as a motion period, a period in which the amount of the temporal change of the three-dimensional position of the living body 50 estimated by the position estimation processor 430 or the amount of the temporal change of the RCS value calculated by the RCS calculator 440 is larger than a predetermined value. Note that FIG. 5 is a graph for explaining an example of extracting a motion period from time series data of the height position (Height) or the RCS value.

When extracting a motion period using the height position, which is the vertical position, or the RCS value, for example, the motion period extractor 451 may use, in order to avoid the influence of instantaneous noises, for example, a median filter, an FIR filter, or average values for the time series data of the obtained three-dimensional position or RCS value to remove noise components in the height position and the RCS value, and may extract as a motion period of the living body, a changing section of the height information or a RCS changing section after filtering. In other words, the motion period extractor 451 may extract a motion period using time series data obtained by removing instantaneous noise components using a predetermined filter from multiple vertical positions or multiple RCS values obtained in time series. FIG. 5 illustrates, for example, a state where the height position and the RCS value were measured using measurement data of a measurement period of about 0.6 seconds and subjected to a predetermined filtering processing, and a state of extracting a motion period. Note that although the motion period extractor 451 is effective to limit a period to be used for the estimation for the purpose of reducing the calculation amount or the like, the motion period extractor 451 is not always necessary. In other words, it goes without saying that in the case of estimating the state for the entire section, the motion period extractor 451 may be eliminated and the entire section may be used for the estimation.

Figure 6:
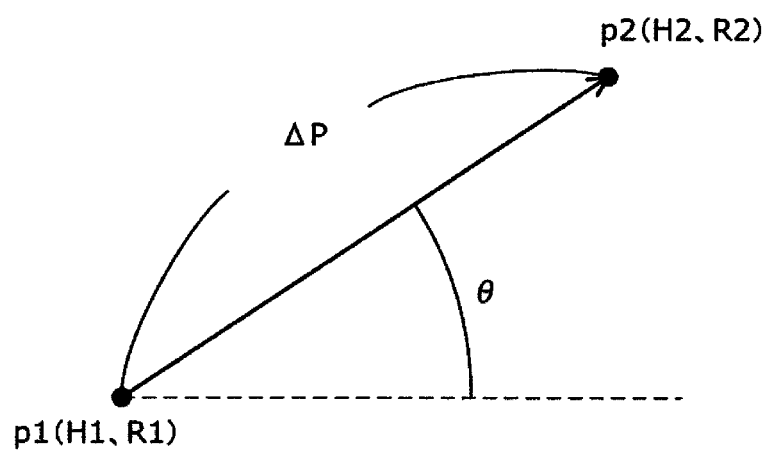
FIG. 6 is a diagram for explaining processing for direction vector conversion.

The direction code calculator 452 converts the temporal changes of the vertical position (height position) obtained from the estimated three-dimensional position and the calculated RCS value during the motion period extracted by the motion period extractor 451, into a direction vector using a predetermined method. Specifically, the direction code calculator 452 two-dimensionally plots height positions and RCS values as illustrated in FIG. 6 and calculates distance $\Delta P$ and direction $\theta$ of the trace indicating the temporal change of the plotted points. For example, the direction code calculator 452 performs direction vector conversion by calculating distance $\Delta P$ between first coordinates p1(H1,R1) and second coordinates p2(H2,R2) and direction $\theta$ of second coordinates p2(H2,R2) viewed from first coordinates p1(H1, R1) from the trace from first coordinates p1(H1,R1) indicated by height position H1 and RCS value R1 at a first timing to second coordinates p2(H2,R2) indicated by height position H2 and RCS value R2 at a second timing which is the next timing to the first timing. FIG. 6 is a diagram for explaining the processing for the direction vector conversion.

Figure 7:
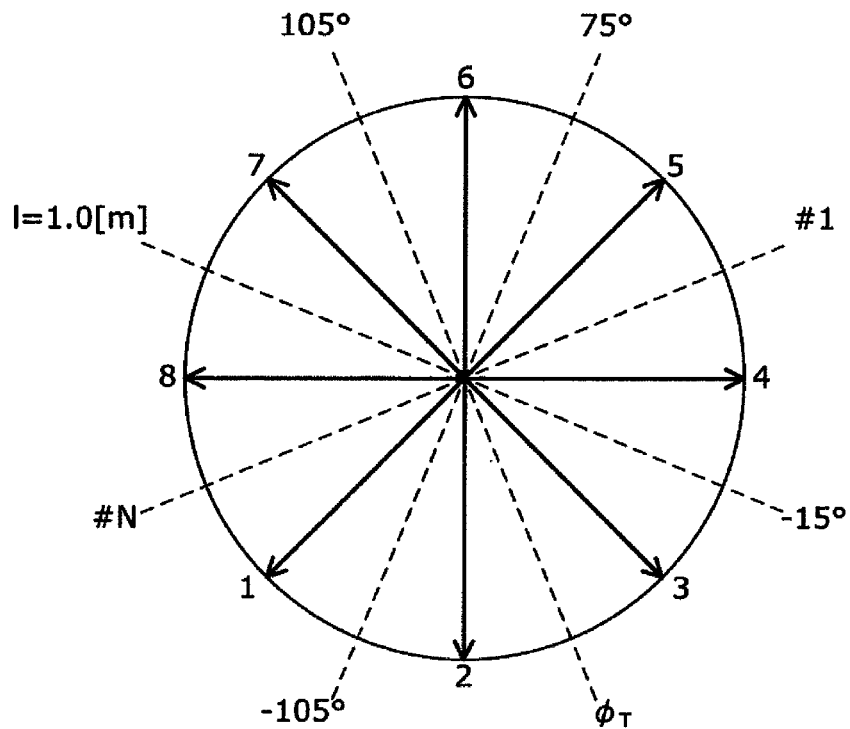
FIG. 7 is a diagram illustrating an example of a direction code chart.

Next, the direction code calculator 452 normalizes the converted direction vector to calculate a direction code. Specifically, the direction code calculator 452 calculates a direction code by referring to a direction code chart illustrated in FIG. 7. For example, the direction code calculator 452 identifies the direction code closest to direction $\theta$ out of the direction codes indicated by 1 to 8. FIG. 7 is a diagram illustrating an example of the direction code chart.

Figure 8:
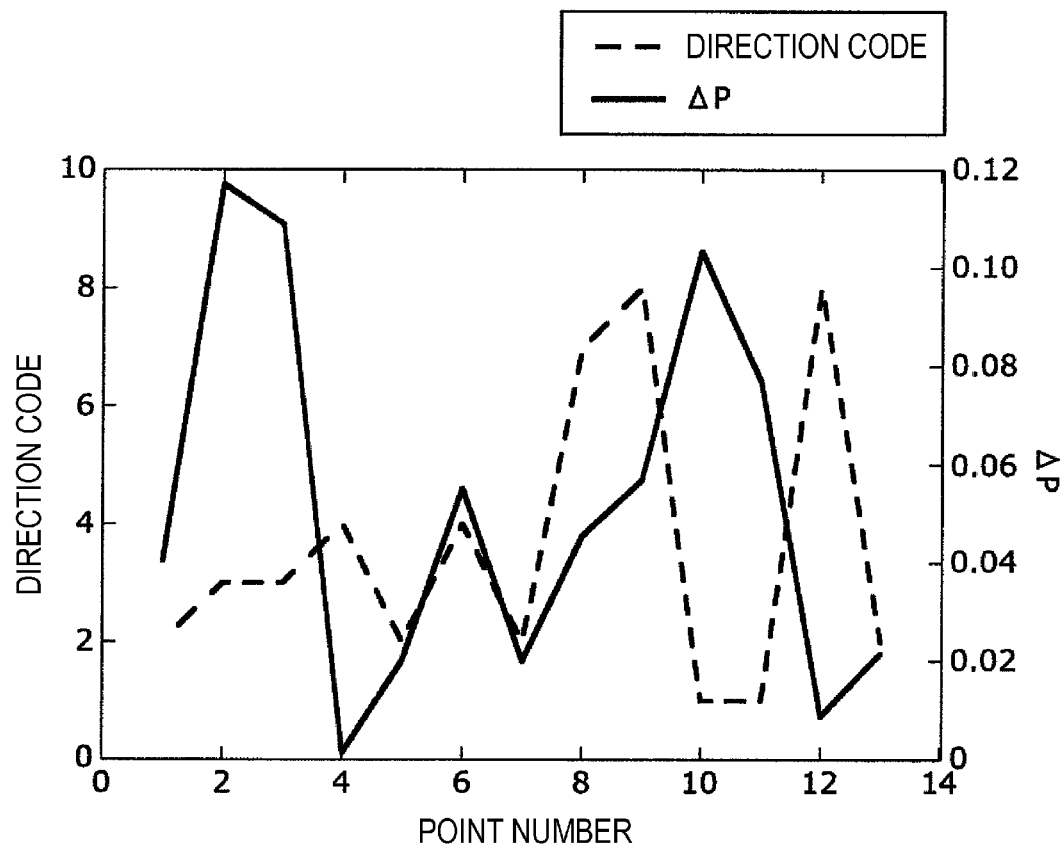
FIG. 8 is a graph illustrating an example of time series data of calculated direction codes and distances.

The direction code calculator 452 obtains time series data of direction codes as illustrated in FIG. 8 by calculating direction codes and distances $\Delta P$ as described above. FIG. 8 is a graph illustrating an example of time series data of calculated direction codes and distances. Note that at this time, the direction code calculator 452 may normalize direction codes to avoid the influence of individual difference.

The motion comparator 453 compares the time series data of direction codes calculated by the direction code calculator 452 with the correspondence information 42 stored in the memory to identify a motion associated with the time series data in the correspondence information 42, and thus estimates a motion of the living body 50.

Figures 9, 10:
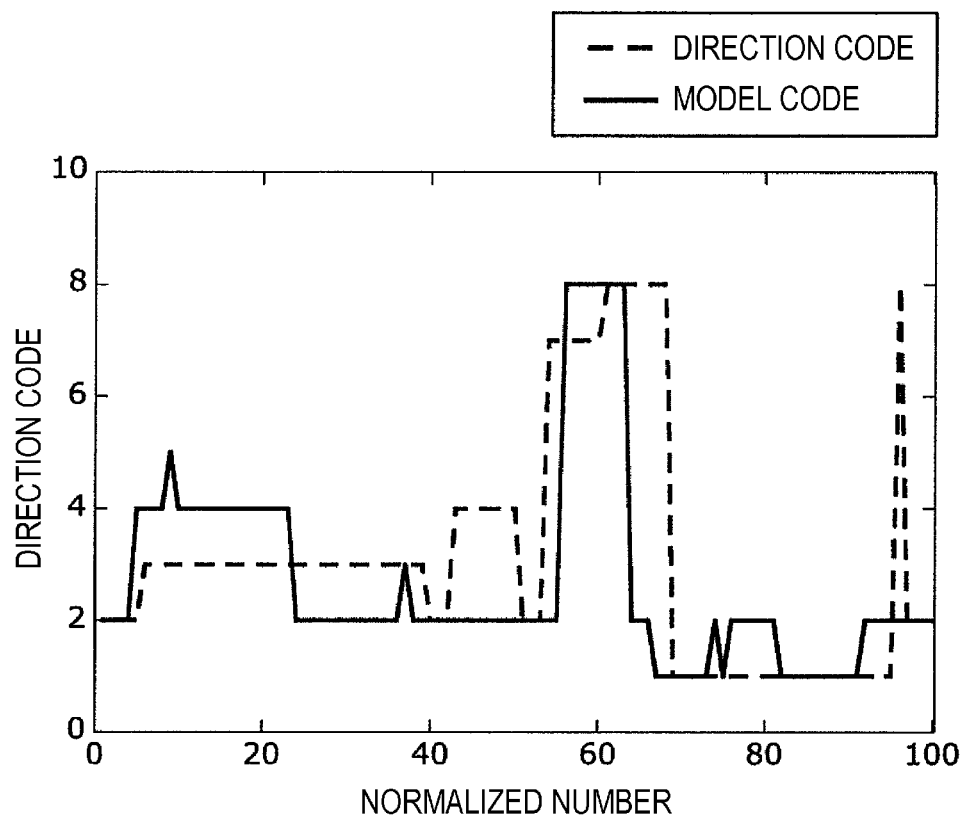
FIG. 9 illustrates a table illustrating an example of correspondence information.
FIG. 10 is a graph illustrating test data obtained from measurement and model data which are model codes.

Note that the correspondence information 42 stored in the memory 41 is information indicating the correspondence between a motion of the living body 50 and multiple model codes indicating the temporal changes of the RCS value and the vertical position which is a position of the living body 50 in the vertical direction relative to the sensor 10. The motions of the living body 50 associated in the correspondence information 42 include falling down, sitting on a chair, sitting on a floor, standing up from a chair, standing up from a floor, jumping, and turning direction, as illustrated in FIG. 9. In other words, the motion estimator 450 estimates which one of the motions, falling down, sitting on a chair, sitting on a floor, standing up from a chair, standing up from a floor, jumping, and turning direction, the living body 50 did, using temporal changes of the three-dimensional position estimated by the position estimation processor 430 and the RCS value calculated by the RCS calculator 440, and the correspondence information 42 stored in advance in the memory 41. Note that the model code is expressed as time series data as illustrated in FIG. 10.

Note that the circuit 40 repeatedly performs the foregoing processing at the sections 410 to 450 at multiple different timings to obtain the time series data. For example, the circuit 40 repeatedly performs processing at a predetermined sampling frequency as described using FIG. 4A or FIG. 4B to obtain time series data including multiple three-dimensional positions in time series and multiple RCS values in time series.

Next, the operation principle of the sensor 10 of the embodiment will be described in detail using mathematical formulae. Note that here described is a method of extracting living body components using Fourier transformation. The processing described here is performed by the circuit 40. In the case where L people are present at an indoor environment, the transmitting antenna 20 is a planar array antenna including $M_T$ elements, and the receiving antenna 30 is a planar array antenna including $M_R$ elements, the measured $M_R \times M_T$ time varying MIMO channel H(t) is expressed as the following Formula 1.

$$H(t) = \begin{pmatrix} h_{11}(t) & \cdots & h_{2M_T}(t) \\ \vdots & \ddots & \vdots \\ h_{M_R1}(t) & \cdots & h_{M_RM_T}(t) \end{pmatrix} \quad \text{(Formula 1)}$$

Here, t is a measurement time, and $h_{ij}$ which is a (i,j)-th element is the channel response from a j-th transmitting antenna element 21 to an i-th receiving antenna element 31.

The $M_R \times M_T$ MIMO array can be converted into a MIMO virtual array expressed in $M_RM_T \times 1$ SIMO (Single-Input Multiple-Output) configuration. Here, $M_R \times M_T$ MIMO channel h(t) is converted into an $M_RM_T \times 1$ virtual SIMO channel which is expressed by the following Formula 2.

$$h(t) = [h_{11}(t), \ldots, h_{M_R1}(t), h_{12}(t), \ldots, h_{M_R2}(t), \ldots, h_{1M_T}(t), \ldots, h_{M_RM_T}(t)]^T \quad \text{(Formula 2)}$$

Here, $\{\bullet\}^T$ indicates transposition. Here, using time difference T, difference channel $h_{sb}(t,T)$ is defined as the following Formula 3.

$$h_{sb}(t,T) = h(t+T) - h(t) \quad \text{(Formula 3)}$$

Although an actual complex channel includes reflection waves not via the living body, such as direct waves and reflection waves derived from stationary objects, all the reflection waves not via the living body are cancelled in a difference channel matrix by subtraction operation. Thus, the complex channel includes only reflection waves derived from the living body.

Here, using difference channel $h_{sb}(t,T)$, instantaneous correlation matrix R(t,T) of difference time T at a measurement time t is defined as the following Formula 4.

$$R(t,T) = h_{sb}(t,T) h_{sb}(t,T)^H \quad \text{(Formula 4)}$$

Here, $\{\bullet\}_H$ indicates complex conjugate transposition. Although the rank of this instantaneous correlation matrix is 1, it is possible to increase the rank of the correlation matrix by average operation, and this makes it possible to perform simultaneous estimation on multiple incoming waves.

Next, descriptions will be provided for a method of three-dimensional direction estimation of the living body, using the correlation matrix obtained from the difference channel matrix. Here, an estimation method based on MUSIC algorithm will be described. The above correlation matrix R is expressed as the following Formulae 5 to 7 by eigenvalue decomposition.

$$R = U \wedge U^H \quad \text{(Formula 5)}$$

$$U = [u_1, \ldots, u_L, u_{L+1}, \ldots, u_{M_RM_T}] \quad \text{(Formula 6)}$$

$$\wedge = \text{diag}[\lambda_1, \ldots, \lambda_L, \lambda_{L+1}, \ldots, \lambda_{M_RM_T}] \quad \text{(Formula 7)}$$

Here, U is an eigenvector, $\wedge$ is an eigenvalue corresponding to the eigenvector, which is in the order indicated by the following Formula 8.

$$\lambda_1 \geq \lambda_2 \geq \ldots \geq \lambda_L \geq \lambda_{L+1} \geq \ldots \geq \lambda_{M_RM_T} \quad \text{(Formula 8)}$$

L is the number of incoming waves, in other words, the number of living body to be detected. In the following description, it is assumed that the distance to the living body to be detected is relatively small compared to the aperture of the array antenna included in the transmitting antenna 20 or the receiving antenna 30. Hence, it is assumed that the array antenna receives spherical waves. Note that even if the distance to the living body to be detected is sufficiently far, the following formulae hold true, and thus there is no problem in detection. In the case where it is known that the distance to the target is sufficiently far, the position of the target may be estimated using departure angle $\theta_T$ and arrival angle $\theta_R$, which would provide an advantage that the calculation is relatively simple. The steering vector of the array antenna on the transmitting antenna 20 side is defined as the following Formulae 9 to 11.

$$\alpha_T(x, y, z) = \left[\exp(-j\Phi_{11}), \ldots, \exp(-j\Phi_{n_x1}), \exp(-j\Phi_{12}), \ldots, \exp(-j\Phi_{n_x2}), \ldots, \exp(-j\Phi_{n_xn_y})\right]^T \quad \text{(Formula 9)}$$

$$\Phi_{n_xn_y} = \frac{2\pi(d_{n_{xc}n_{yc}} - d_{n_xn_y})}{\lambda} \quad \text{(Formula 10)}$$

$$d_{n_xn_y} = \sqrt{(x - dx_{n_x})^2 + (y - dy_{n_y})^2 + (z - dz_{n_z})^2} \quad \text{(Formula 11)}$$

Similarly, the steering vector of the array antenna on the receiving antenna 30 side is defined as the following Formulae 12 to 14.

$$\alpha_R(x, y, z) = \left[\exp(-j\Theta_{11}), \ldots, \exp(-j\Theta_{m_x1}), \exp(-j\Theta_{12}), \ldots, \exp(-j\Theta_{m_x2}), \ldots, \exp(-j\Theta_{m_xm_y})\right]^T \quad \text{(Formula 12)}$$

$$\Theta_{m_xm_y} = \frac{2\pi(d_{m_{xc}m_{yc}} - d_{m_xm_y})}{\lambda} \quad \text{(Formula 13)}$$

$$d_{m_xm_y} = \sqrt{(x - dx_{m_x})^2 + (y - dy_{m_y})^2 + (z - dz_{m_z})^2} \quad \text{(Formula 14)}$$

Here, $d_{mxmy}$ and $d_{nxny}$ are the distances between a wave source, in other words, the living body, and $m_xm_y$-th and $n_xn_y$-th array elements, respectively; $d_{mxcmyc}$ and $d_{nxcnyc}$ are the distances between the wave source and reference elements; $\Theta_{nxny}$, $\Phi_{nxny}$ are the phase delays; and $\lambda$ is the wavelength.

Further, by multiplying the steering vectors of transmission and reception together, a steering vector considering angle information of both transmission and reception is defined as illustrated in the following Formula 15.

$$\alpha(x,y,z) = \text{vec}(\alpha_R(x,y,z)\alpha_T^T(x,y,z)) \quad \text{(Formula 15)}$$

Applying MUSIC method to this, the direction of an incoming wave is estimated by searching for a local maximum value of the evaluation function expressed by the following Formula 16, using this steering vector.

$$P_{music}(x, y, z) = \frac{1}{|a^H(x, y, z)[u_{L+1}, \ldots, w_{M_R M_T}]|^2} \quad \text{(Formula 16)}$$

Here, three dimensional search processing is executed because this search is performed on coordinates (x, y, z) of a space.

Further, the Rader Cross Section (RCS) from the living body is calculated using position information (x, y) obtained from the search.

Using frequency response matrix $F(\omega)$ obtained by Fourier transforming measured propagation channel matrix $H(t)$ and vectorizing the resultant, reception electric power $P_\gamma(\omega)$ is expressed as the following Formula 17.

$$P_\gamma(\omega) = F(\omega)F(\omega)^H \quad \text{(Formula 17)}$$

Here, scattering cross section $\sigma$ of the living body is expressed as the following Formulae 18 to 20.

$$\sigma = \frac{(4\pi)^2 R_R^2 R_T^2}{G_R G_T \lambda^2} \frac{\int_{\omega_1}^{\omega_2} P_T(\omega) d\omega}{P_t} \quad \text{(Formula 18)}$$

$$R_R = \sqrt{(x - x_R)^2 + (y - y_R)^2} \quad \text{(Formula 19)}$$

$$R_T = \sqrt{(x - x_T)^2 + (y - y_T)^2} \quad \text{(Formula 20)}$$

Here, $R_R$ is the distance from the receiving antenna 30 to the estimated position of the living body 50, and $R_T$ is the distance from the transmitting antenna 20 to the estimated position of the living body 50. $G_R$ is the gain of the receiving antenna 30, and $G_T$ is the gain of the transmitting antenna 20. In addition, $\omega_1$ of is the minimum frequency of biological activities, and $\omega_2$ is the maximum frequency of the biological activities.

As described above, by extracting the only components of the frequencies corresponding to biological activities, it is possible to extract only electric power reflected by the living body. The body surface area viewed from the antenna is different depending on the posture of the living body, so that it is possible to estimate the state of the living body. In addition to it, the action of the living body increases the frequency components caused by the body motion, resulting in the variation of RCS, so that by modeling the trace of the estimated height z and Rader Cross Section $\sigma$ of the living body, it is possible to estimate the motion of the living body.

A method of motion estimation will be described below.

With the method described above, it is possible to measure the trace of $\sigma$-z characteristic by estimating scattering cross section $\sigma$ and height z of the living body continuously at multiple different timings. Here, since when the living body is at rest, there is almost no change in the RCS value, a flow of trace points in which the living body is in motion, in other words, in which the variation of the RCS value is large is extracted. As for the group of trace points, when $\Delta P_i$ is a trace point movement amount which is the distance between an (i−1)-th trace point and an i-th trace point, and $\alpha_i$ is an angle parameter which is the angle formed between the (i−1)-th trace point and the i-th trace point, $\Delta P_i$ and $\alpha_i$ are defined by the following Formulae 21 and 22, respectively.

$$\Delta P_i = \sqrt{(\sigma_i - \sigma_{i-1})^2 + (z_i - z_{i-1})^2} \quad \text{(Formula 21)}$$

$$\alpha_i = \tan^{-1}\left(\frac{z_i - z_{i-1}}{\sigma_i - \sigma_{i-1}}\right) \quad \text{(Formula 22)}$$

Next, using the value of the angle parameter, a direction code is assigned to the moving direction of a trace point. To assign a direction code to an angle, 360° is divided into 8 angles, to each of which the number of 1 to 8 is assigned. In this case, to prevent the code from changing very often for movement in the vertical direction and the horizontal direction, it is also possible not to set the boundary of codes in these directions. Since there are individual differences in the speed of movement, normalization of direction codes may be performed considering the difference in the speed of motion to avoid erroneous recognition caused because the number of trace points differs due to the speed of motion even though the motion is the same. For example, from original direction code string c(j=1 to $j_{max}$) obtained by the direction estimation, a normalized code string having K terms is generated considering the ratio of the trace point movement amount to the sum of the trace point movement amounts. Here, $j_{max}$ is the number of trace points, which is different depending on the motion time. Normalized code string $C_k$(k=1, 2, ..., K) is generated from i-th trace movement amount $\Delta P_i$ and the sum of trace point movement amounts $\Delta P_{sum}$ as follows.

1) When j=1, the normalized code string in which k is within the range satisfying the following Formula 23 is the original direction code string with j=1.

$$1 \le k \le \frac{\Delta P_1}{\Delta P_{sum}} \times K \quad \text{(Formula 23)}$$

2) when j is within the range of 2 to $j_{max}$, the normalized code string in which k is within the range satisfying the following formula 24 is the code with each j. Here, $\Delta P_{sum}$ satisfies the following Formula 25.

$$\sum_{i=1}^{i-1} \Delta P_i \times K < k \le \frac{\sum_{i=1}^{i} \Delta P_i}{\Delta P_{sum}} \times K \quad \text{(Formula 24)}$$

$$\Delta P_{sum} = \sum_{i=1}^{i_{max}} \Delta P_i \quad \text{(Formula 25)}$$

For the motion estimation, a normalized number sequence (test data) having K items made from the trace points is compared with model data number sequences with K items each corresponding to one of the multiple motions. As for the model data number sequence, multiple measurements are conducted in advance while each of the multiple motions is performed, and the most frequent direction code among items in the normalized code string obtained from the multiple motion measurements is set as model data for the item. Since the direction codes are circular, the maximum difference is 4. To calculate the difference between a direction code number and actual one, the following Formula 26 is used. Here, when $\delta C_i > 4$, the following Formula 27 is used.

$$\delta C_i = |C_{test,i} - C_{model,i}| \quad \text{(Formula 26)}$$

$$\delta C_i = 8 - \delta C_i \quad \text{(Formula 27)}$$

Here, $C_{test,i}$ is the element at the i-th item of the test data string, and $C_{model,i}$ is the element at the i-th item of the model data string. Next, the sum of squares of the direction code difference between the test data and the model data is calculated as a deviation expressed by the following Formula 28. For example, as illustrated in FIG. 10, the test data and the model data are compared with each other to calculate the deviation. FIG. 10 is a graph illustrating test data obtained from measurement and model data which are model codes.

$$E = \delta C_1^2 + \delta C_2^2 + \ldots + \delta C_K^2 \quad \text{(Formula 28)}$$

Then, the motion corresponding to the model data string of which the deviation is the smallest is outputted as a recognition result.

Next, operation of sensor 10 according to the embodiment will be described using a flowchart.

Figure 11:
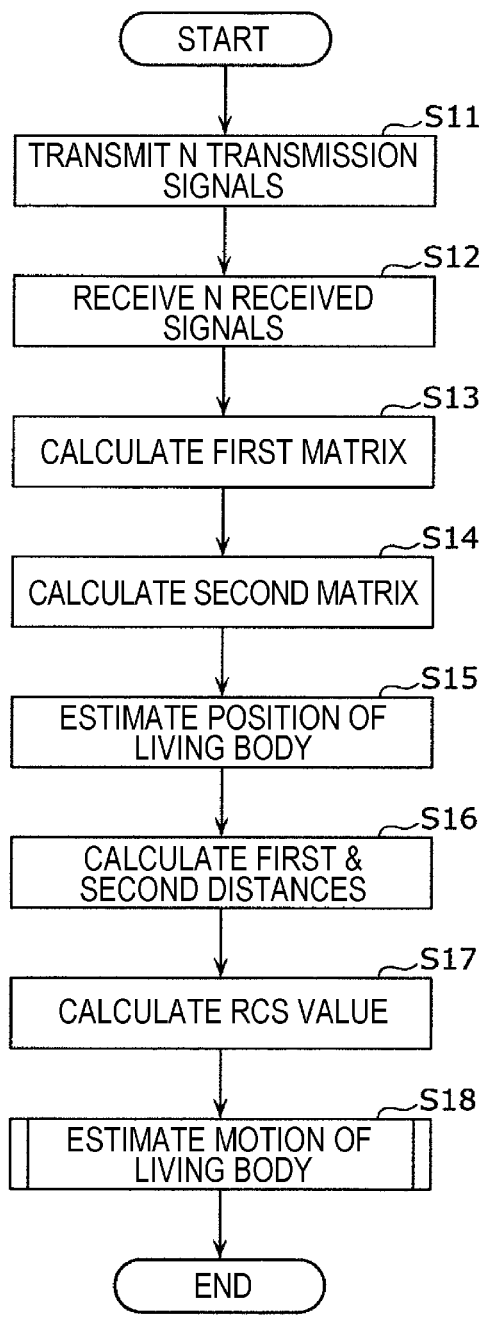
FIG. 11 is a flowchart illustrating an example of operation of the sensor according to the embodiment.

FIG. 11 is a flowchart illustrating an example of operation of the sensor according to the embodiment.

In the sensor 10, the N transmitting antenna elements 21 of the transmitting antenna 20 transmit N transmission signals to a specified area where the living body 50 can be present, using the N transmitting antenna elements 21 (S11).

The M receiving antenna elements 31 of the receiving antenna 30 receive N received signals including multiple reflection signals which the living body 50 generates by reflecting the N transmission signals transmitted by the transmitting antenna 20 (S12).

The circuit 40 calculates the N×M first matrix the components of which are complex transfer functions each indicating a propagation property between each of the N transmitting antenna elements 21 and each of the M receiving antenna elements 31, from each of the N received signals received by each of the M receiving antenna elements 31 during the specified period (S13).

The circuit 40 extracts the second matrix corresponding to the specified frequency range in the first matrix. The extracted second matrix corresponds to components affected by vital activities including at least one of respiration, heartbeats, and body motion of the living body 50 (S14).

Using the second matrix, the circuit 40 estimates the three-dimensional position at which the living body 50 is present, relative to the sensor 10 (S15).

The circuit 40 calculates distance r1 indicating the distance between the living body 50 and the transmitting antenna 20 and distance r2 indicating the distance between the living body 50 and the receiving antenna 30, based on the estimated three-dimensional position, the position of the transmitting antenna 20, and the position of the receiving antenna 30 (S16).

The circuit 40 calculates the RCS value of the living body 50, using the first distance and the second distance (S17).

The circuit 40 estimates the motion of the living body 50, using the calculated RCS value and the information 42 stored in the memory 41 indicating correspondence between the RCS value and the motion of the living body 50 (S18).

Next, the estimation processing for estimating the motion of the living body 50 will be described in detail.

Figure 12:
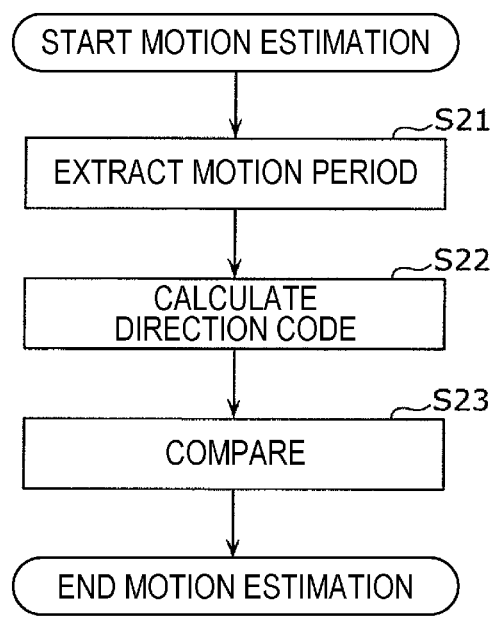
FIG. 12 is a flowchart illustrating an example of details of estimation processing.

FIG. 12 is a flowchart illustrating an example of details of the estimation processing.

The circuit 40 extracts a period in which the temporal change of the vertical position of the estimated three-dimensional position or the calculated RCS value is larger than a predetermined value, as a motion period in which the living body 50 is in motion (S21).

The circuit 40 converts the temporal changes of the vertical position obtained from the estimated three-dimensional position and the calculated RCS value during the extracted motion period into a direction vector, using a predetermined method, and normalizes the direction vector obtained from the conversion to calculate the direction code (S22).

The circuit 40 compares the time series data of the calculated direction codes with the correspondence information 42 stored in the memory and identifies the motion associated with the time series data in the correspondence information 42 to estimates the motion of the living body 50 (S23).

Next, prior learning operation of the sensor 10 for acquiring the correspondence information 42 will be described.

Figure 13:
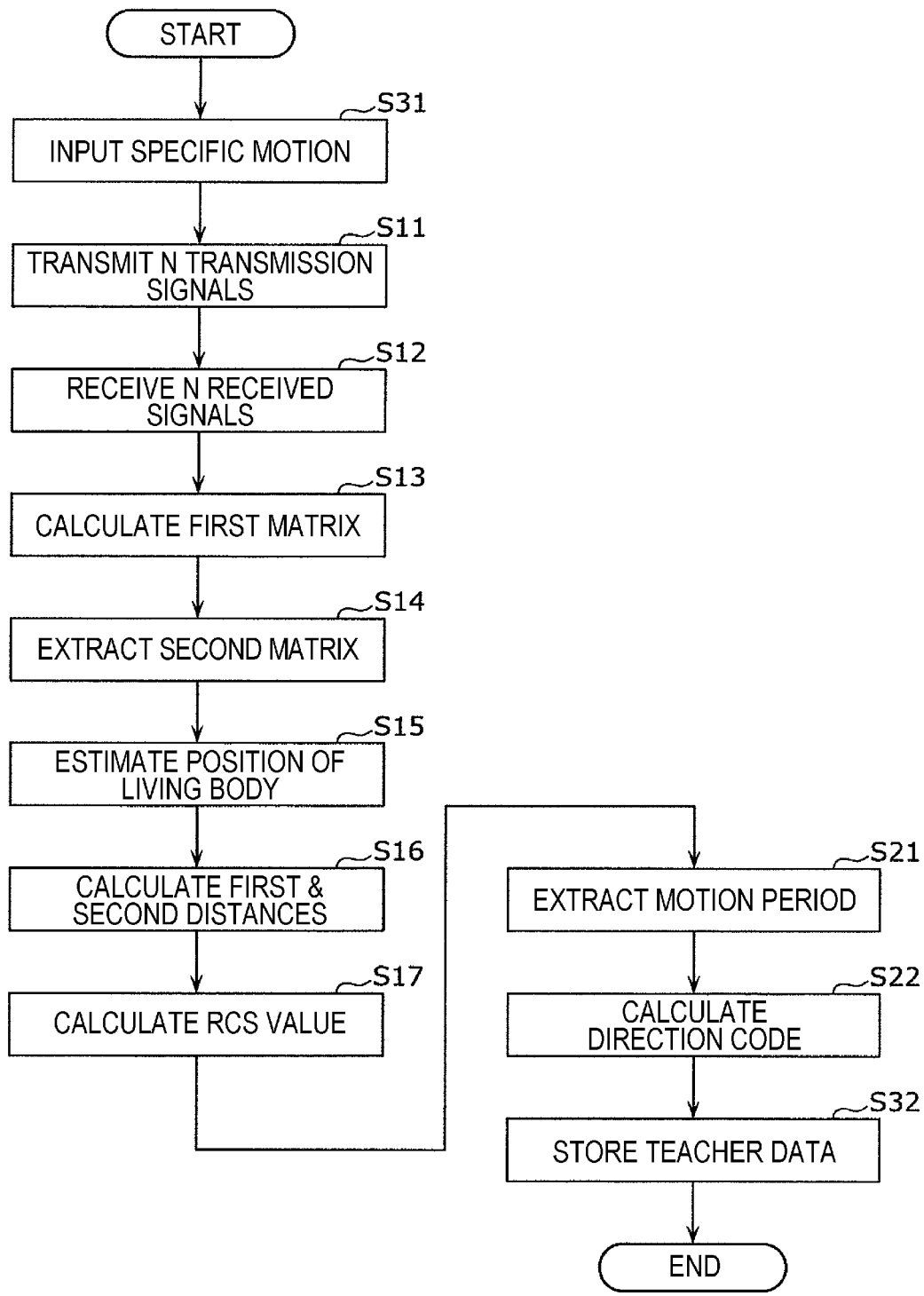
FIG. 13 is a flowchart illustrating an example of operation of the sensor in prior learning processing.

FIG. 13 is a flowchart illustrating an example of operation of the sensor in the prior learning processing.

The circuit 40 receives input for specifying a specific motion with non-illustrated input means (S31). This allows the circuit 40 to recognize that the motion performed during a predetermined period is the motion indicated by the received input.

Next, the same processing as in steps S11 to S17 and steps S21 and S22 of the operation of the sensor 10 described above is executed sequentially.

Next, the circuit 40 stores the correspondence information obtained by associating the motion indicated by the input received at step S31 with the time series data of the calculated direction codes, as teacher data in the memory 41 (S32).

The sensor 10 according to the embodiment is capable of estimating the position where the living body 50 is present and the motion of the living body at the position in a short time with high accuracy.

The sensor 10 detects a part in motion to detect the existence of the living body 50. Thus, utilizing this, for example, makes it possible to estimate which one of the motions that a living human is performing, the motions being falling down, sitting on a chair, sitting on a floor, standing up from a chair, standing up from a floor, jumping, and turning direction. This makes it possible to check the existence of a human effectively. In addition, since it is possible to check the existence of a human without image analysis of an image captured by a camera, the existence of a human can be checked with the privacy of the human protected.

Although the sensor 10 according to one or more aspects of the present disclosure has been described based on the embodiment as above, the present disclosure is not limited to this embodiment. Unless departing from the spirit of the present disclosure, one in which various modification occurring to those skilled in the art are applied to this embodiment and an embodiment made by combining constituents from different embodiments may be included within the one or more aspects of the present disclosure.

Although, in the above embodiment, the correspondence information 42 of the sensor 10 is information in which model codes, which the vertical positions and the RCS values are converted into direction codes, are associated with motions, the correspondence information 42 is not limited to this. For example, information in which the temporal changes of the vertical position and the RCS value without any conversion are associated with motions may be used as correspondence information. In this case, the motion estimator 450 of the circuit 40 does not need to include the direction code calculator 452.

According to the above embodiment, the circuit 40 of the sensor 10 may estimate, using the estimated motion, the motion performed next by the living body 50. In other words, the circuit 40 may estimate the motion of the living body 50 in the second motion period next to the first motion period, using the posture of the living body 50 when the first motion period ends. For example, when the circuit 40 estimates that the living body 50 stood up, it is apparent that the living body 50 is already in a standing position. Hence, judging that the living body 50 cannot stand up next, the circuit 40 may exclude, in comparing using the correspondence information 42, the motion of standing up from the motions to be compared in the correspondence information 42. This makes it possible to estimate the motion of the living body 50 with high accuracy.

In the above embodiment, the sensor 10 estimate the motion of the living body 50 from the data obtained using microwaves, usage of the sensor 10 is not limited to estimating motions.

For example, the circuit 40 of the sensor 10 may determine whether the variation in the horizontal direction is larger than or equal to a predetermined distance from the time series data of the three-dimensional position of the living body 50, and if the variation is larger than or equal to the predetermined distance, the circuit 40 may estimate that the living body 50 is moving in the horizontal direction. In this case, if the variation in the horizontal direction is larger than a predetermined threshold, the circuit 40 may estimate that the living body 50 is running. If it is smaller than the predetermined threshold, the circuit 40 may estimate that the living body 50 is walking. This method makes it possible to estimate the movement of the living body 50 in the horizontal direction in a short time with high accuracy.

In addition, for example, the circuit 40 of the sensor 10 may further estimate the height of the living body 50, using the vertical position included in the three-dimensional position when the living body 50 is estimated to be moving in the horizontal direction. Specifically, in this case, the circuit 40 may estimate the height of the living body 50 by multiplying the obtained vertical position by a predetermined coefficient. As described above, since, for example, the vertical position of the abdominal part is obtained as the vertical position of the living body 50, the height of the living body 50 can be estimated by multiplying the vertical position of the abdominal part by a coefficient within the rage of 1.5 to 2.0 as a predetermined coefficient, for example. Note that the height is estimated by multiplication of a predetermined coefficient as above based on the assumption that when the living body 50 is moving in the horizontal direction, a human who is the living body 50 is in a standing position.

Thus, for example, if multiple living bodies which can be present in a specified area are known in advance, and the heights of the multiple living bodies are different, this method can be utilized to identify which living body of the multiple living bodies is present and in motion. For example, if the specified area is a room in a house, and people who are living in the house are limited, this method can be utilized to identify who of the people living in the house the obtained living body 50 is, by comparing an obtained vertical position with the heights of the people living in the house.

In addition, the circuit 40 of the sensor 10 may further estimate, for example, the body size of the living body 50, using the RCS value when the living body 50 is estimated to be moving in the horizontal direction. If multiple living bodies which can be present in a specified area are known in advance, and the body sizes of the multiple living bodies are different, this method can be utilized, for example, to identify which living body of the multiple living bodies is present and in motion. In other words, similarly to the case of height, it is possible to utilize the method to identify who is present.

The present disclosure can be utilized for sensors and methods for estimating the directions and the positions of moving objects using microwaves. In particular, the present disclosure can be utilized for measurement instruments for measuring the directions and the positions of moving objects including living bodies and mechanical objects, home appliances which perform control in accordance with the directions and the positions of the moving objects, direction estimation methods and position estimation methods used in monitoring apparatuses or the like for detecting intrusion of a moving object, and height estimation apparatuses using the Rader Cross Section.

What is claimed is:

1. A sensor, comprising:
    a transmitting antenna including N transmitting antenna elements, each of which transmits a transmission signal to a specified area where a living body can be present, N being a natural number of 3 or more;
    a receiving antenna including M receiving antenna elements, each of which receives N received signals including a reflection signal that the living body generates by reflecting part of the N transmission signals transmitted by the N transmitting antenna elements, M being a natural number of 3 or more;
    a circuit; and
    a memory that stores correspondence information indicating correspondence of a motion of the living body with temporal changes of a radar cross-section value and a vertical position, which is a position in a vertical direction at which the living body is present relative to the sensor, wherein
    at least two transmitting antenna elements of the N transmitting antenna elements are arranged in positions in which the vertical position is different from each other,
    at least two transmitting antenna elements of the N transmitting antenna elements are arranged in positions in which a horizontal position is different from each other,
    at least two receiving antenna elements of the M receiving antenna elements are arranged in positions in which a vertical position is different from each other,
    at least two receiving antenna elements of the N transmitting antenna elements are arranged in positions in which the horizontal position is different from each other, and
    the circuit
        calculates an N×M first matrix with components, each of which is a complex transfer function indicating a propagation property between each of the N transmitting antenna elements and each of the M receiving antenna elements, from each of the N received signals received by each of the M receiving antenna elements during a specified period,
        extracts a second matrix corresponding to a specified frequency range in the first matrix, the second matrix corresponding to components affected by a vital activity including at least one of respiration, heartbeats, and body motion of the living body,
        estimates a three-dimensional position at which the living body is present relative to the sensor, using the second matrix, the three-dimensional position including the vertical position, calculates a first distance indicating a distance between the living body and the transmitting antenna and a second distance indicating a distance between the living body and the receiving antenna, based on the estimated three-dimensional position, a position of the transmitting antenna, and a position of the receiving antenna, calculates a radar cross-section value of the living body, using the first distance and the second distance, and estimates a motion of the living body, using temporal changes of the estimated three-dimensional position and the calculated radar cross-section value, and the correspondence information stored in the memory.

2. The sensor according to claim 1, wherein the motion of the living body associated in the correspondence information includes falling down, sitting on a chair, sitting on a floor, standing up from a chair, standing up from a floor, jumping, and turning direction, and the circuit estimates which motion the living body is performing, out of the falling down, sitting on a chair, sitting on a floor, standing up from a chair, standing up from a floor, jumping, and turning direction, using the temporal changes of the estimated three-dimensional position and the calculated radar cross-section value and the correspondence information stored in the memory.

3. The sensor according to claim 1, wherein in estimating the motion of the living body, the circuit extracts a period in which the temporal change of the estimated vertical position or the calculated radar cross-section value is larger than a predetermined value, as a motion period in which the living body is in motion, and estimates the motion of the living body, using the temporal changes of the estimated three-dimensional position and the calculated radar cross-section value during the extracted motion period, and the correspondence information stored in the memory.

4. The sensor according to claim 3, wherein the circuit extracts the motion period, using time series data obtained from a plurality of the vertical positions or a plurality of the radar cross-section values obtained in time series by removing an instantaneous noise component using a predetermined filter.

5. The sensor according to claim 3, wherein the vertical position and the radar cross-section value which are associated with the motion of the living body in the correspondence information are expressed by a direction code which is obtained by normalizing a direction vector into which the temporal changes of the vertical position estimated by the circuit and the radar cross-section value calculated by the circuit in advance when the living body performs one motion as the motion of the living body in the specified area are converted by using a predetermined method, and in estimating the motion of the living body, the circuit converts the temporal changes of the vertical position obtained from the estimated three-dimensional position and the calculated radar cross-section value during the extracted motion period into a direction vector using a predetermined method, calculates a direction code by normalizing the direction vector obtained from conversion, and estimates the motion of the living body using the calculated direction code and the corresponding information.

6. The sensor according to claim 1, wherein the circuit estimates the motion of the living body during a second motion period next to a first motion period, using a posture of the living body at the end of the first motion period.

7. The sensor according to claim 1, wherein when a variation in a horizontal direction of the estimated three-dimensional position is larger than or equal to a predetermined distance, the circuit further estimates that the living body is moving in the horizontal direction.

8. The sensor according to claim 7, wherein the circuit further estimates a height of the living body, using the vertical position included in the three-dimensional position from which the living body is estimated to be moving in the horizontal direction.

9. The sensor according to claim 7, wherein the circuit further estimates a body size of the living body, using the radar cross-section value calculated when the living body is estimated to be moving in the horizontal direction.

10. The sensor according to claim 1, wherein the specified period is about half a cycle of at least one of respiration, heartbeats, and body motion of the living body.

11. A method of estimating a motion of a living body using a sensor, the sensor comprising:

a transmitting antenna including N transmitting antenna elements, N being a natural number of 3 or more;

a receiving antenna including M receiving antenna elements, M being a natural number of 3 or more;

a circuit; and a memory that stores correspondence information indicating correspondence among a motion of a living body, a radar cross-section value, and a vertical position, which is a position in a vertical direction at which the living body is present relative to the sensor, wherein at least two transmitting antenna elements of the N transmitting antenna elements are arranged in positions different in the vertical direction, at least two transmitting antenna elements of the N transmitting antenna elements are arranged in positions different in a horizontal direction, at least two receiving antenna elements of the M receiving antenna elements are arranged in positions different in the vertical direction, at least two receiving antenna elements of the M receiving antenna elements are arranged in positions different in the horizontal direction, and the method comprises:

transmitting N transmission signals to a specified area where the living body can be present, using the N transmitting antenna elements;

receiving, by using each of the M receiving antenna elements, N received signals including a reflection signal which the living body generates by reflecting part of the transmitted N transmission signals;

calculating an N×M first matrix with components, each of which is a complex transfer function indicating a propagation property between each of the N transmitting antenna elements and each of the M receiving antenna elements, from each of the N received signals received by each of the M receiving antenna elements during a specified period;

extracting a second matrix corresponding to a specified frequency range in the first matrix, the second matrix corresponding to components affected by a vital activity including at least one of respiration, heartbeats, and body motion of the living body;

estimating a three-dimensional position at which the living body is present relative to the sensor, using the second matrix, the three-dimensional position including the vertical position;

calculating a first distance indicating a distance between the living body and the transmitting antenna and a second distance indicating a distance between the living body and the receiving antenna, based on the estimated three-dimensional position, a position of the transmitting antenna, and a position of the receiving antenna;

calculating a radar cross-section value of the living body, using the first distance and the second distance; and estimating a motion of the living body, using temporal changes of the estimated three-dimensional position and the calculated radar cross-section value, and the correspondence information stored in the memory.

12. A sensor, comprising:

a transmitting antenna including N transmitting antenna elements, each of which transmits a transmission signal to a specified area where a living body can be present, N being a natural number of 3 or more;

a receiving antenna including M receiving antenna elements, each of which receives N received signals including a reflection signal which the living body generates by reflecting part of the N transmission signals transmitted by the N transmitting antenna elements, M being a natural number of 3 or more;

a circuit; and a memory that stores correspondence information indicating correspondence of a motion of the living body with temporal changes of a radar cross-section value and a vertical position, which is a position in a vertical direction at which the living body is present relative to the sensor, wherein the N transmitting antenna elements include a first transmitting antenna and a second transmitting antenna that are arranged in a horizontal direction, the N transmitting antenna elements further include a third transmitting antenna, which vertical position is different from vertical position of the first transmitting antenna, the M receiving antenna elements include a first receiving antenna and a second receiving antenna, which are arranged in a horizontal direction, the M transmitting antenna elements further include a third receiving antenna, which vertical position is different from a vertical position of the first receiving antenna, and the circuit calculates an N×M first matrix with components, each of which is a complex transfer function indicating a propagation property between each of the N transmitting antenna elements and each of the M receiving antenna elements, from each of the N received signals received by each of the M receiving antenna elements during a specified period, extracts a second matrix corresponding to a specified frequency range in the first matrix, the second matrix corresponding to components affected by a vital activity including at least one of respiration, heartbeats, and body motion of the living body, estimates a three-dimensional position at which the living body is present relative to the sensor, using the second matrix, the three-dimensional position including the vertical position, calculates a first distance indicating a distance between the living body and the transmitting antenna and a second distance indicating a distance between the living body and the receiving antenna, based on the estimated three-dimensional position, a position of the transmitting antenna, and a position of the receiving antenna, calculates a radar cross-section value of the living body, using the first distance and the second distance, and estimates a motion of the living body, using temporal changes of the estimated three-dimensional position and the calculated radar cross-section value, and the correspondence information stored in the memory.

13. A method of estimating a motion of a living body using a sensor, the sensor comprising:

a transmitting antenna including N transmitting antenna elements, N being a natural number of 3 or more;

a receiving antenna including M receiving antenna elements, M being a natural number of 3 or more;

a circuit; and a memory that stores correspondence information indicating correspondence among a motion of a living body, a radar cross-section value, and a vertical position, which is a position in a vertical direction at which the living body is present relative to the sensor, wherein the N transmitting antenna elements include a first transmitting antenna and a second transmitting antenna that are arranged in a horizontal direction, the N transmitting antenna elements further include a third transmitting antenna, which vertical position is different from a vertical position of the first transmitting antenna, the M receiving antenna elements include a first receiving antenna and a second receiving antenna, which are arranged in a horizontal direction, the M transmitting antenna elements further include a third receiving antenna, which vertical position is different from a vertical position of the first receiving antenna, the method comprises:

transmitting N transmission signals to a specified area where the living body can be present, using the N transmitting antenna elements;

receiving, by using each of the M receiving antenna elements, N received signals including a reflection signal which the living body generates by reflecting part of the transmitted N transmission signals;

calculating an N×M first matrix with components, each of which is a complex transfer function indicating a propagation property between each of the N transmitting antenna elements and each of the M receiving antenna elements, from each of the N received signals received by each of the M receiving antenna elements during a specified period;

extracting a second matrix corresponding to a specified frequency range in the first matrix, the second matrix corresponding to components affected by a vital activity including at least one of respiration, heartbeats, and body motion of the living body;

estimating a three-dimensional position at which the living body is present relative to the sensor, using the second matrix, the three-dimensional position including the vertical position;

calculating a first distance indicating a distance between the living body and the transmitting antenna and a second distance indicating a distance between the living body and the receiving antenna, based on the estimated three-dimensional position, a position of the transmitting antenna, and a position of the receiving antenna;

calculating a radar cross-section value of the living body, using the first distance and the second distance; and estimating a motion of the living body, using temporal changes of the estimated three-dimensional position and the calculated radar cross-section value, and the correspondence information stored in the memory.

* * * * *